US012091376B2

(12) United States Patent
Belter

(10) Patent No.: US 12,091,376 B2
(45) Date of Patent: Sep. 17, 2024

(54) IRON SALT CATALYST REGENERATION

(71) Applicant: Randolph Belter, Zachary, LA (US)

(72) Inventor: Randolph Belter, Zachary, LA (US)

( * ) Notice: Subject to any disclaimer, the term of this patent is extended or adjusted under 35 U.S.C. 154(b) by 0 days.

(21) Appl. No.: 18/049,211

(22) Filed: Oct. 24, 2022

(65) Prior Publication Data

US 2024/0132427 A1  Apr. 25, 2024
US 2024/0228410 A9  Jul. 11, 2024

(51) Int. Cl.
*C07C 17/281* (2006.01)
*B01J 19/24* (2006.01)
*B01J 27/128* (2006.01)
*B01J 31/02* (2006.01)
*B01J 31/20* (2006.01)
*B01J 31/30* (2006.01)
*B01J 31/40* (2006.01)

(52) U.S. Cl.
CPC ............ *C07C 17/281* (2013.01); *B01J 19/24* (2013.01); *B01J 27/128* (2013.01); *B01J 31/0258* (2013.01); *B01J 31/20* (2013.01); *B01J 31/30* (2013.01); *B01J 31/403* (2013.01); *B01J 2231/4205* (2013.01); *B01J 2531/842* (2013.01)

(58) Field of Classification Search
CPC ... C07C 17/281; B01J 27/128; B01J 31/0258; B01J 31/20; B01J 2351/842
See application file for complete search history.

(56) References Cited

U.S. PATENT DOCUMENTS

| 3,471,579 | A | * | 10/1969 | Kubicek | ............... | C07C 17/272 |
| | | | | | | 562/605 |
| 8,722,946 | B2 | | 5/2014 | Close et al. | | |
| 8,835,702 | B2 | | 9/2014 | Close et al. | | |
| 8,912,372 | B2 | | 12/2014 | Wilson et al. | | |
| 2004/0225166 | A1 | | 11/2004 | Wilson et al. | | |

OTHER PUBLICATIONS

Asscher, M and Vofsi, D., Chlorine Activation by Redox Transfer. Part II. The Addition of Carbon Tetrahloride to Olefins, 1963, p. 1887-1896.
Freidlina, Chukovskaya, and Englin, A New Type Of Chain Transfer In Radical Telomerization Using An "Intermediary," Doklady Akademii Nauk USSR, Reports of the Academy of Sciences USSR, 1964. vol. 159, No. 6, p. 1346-1349 (Including machine translation).
Freidlina, Grigor'ev, and Englin, Some Characteristics of Telomerization of Propylene and Ethylene with CCl4, Initiated by Iron Pentacarbonyl, 1973, Bull. Acad. Sci. USSR 22 (2) 323-327.

(Continued)

*Primary Examiner* — Jafar F Parsa
(74) *Attorney, Agent, or Firm* — Edel Patents LLC; John B. Edel

(57) ABSTRACT

Chemical processes are disclosed that act to both regenerate and create new catalyst for iron salt catalyzed Kharasch coupling reactions during the process of creating halogenated hydrocarbons. Such processes include loading a reactor with a quantity of Fe(0) metal such as iron wire, supplying $CCl_4$ to the reactor, supplying a phosphate compound to the reactor, supplying an alkene to the reactor, and supplying a carbonyl of Fe(0) to the reactor.

14 Claims, 1 Drawing Sheet

(56) References Cited

OTHER PUBLICATIONS

Tararov, Savel'eva, Struchkov, Pisarevskii, Raevskii, and Belokon, On the Mechanisim of the Fe(CO) 5-Catalyzed Kharasch Reaction 1. Stereochemistry of addition of BrCCl3 to (R)-3-(E)-cinnamoyl-4-phenyloxazolidin-2-one, (R)-3-(E)-acryloyl-4-phenyloxazolidin-2-one, and their pi-complexes with Fe(CO)4, Mar. 1996, Russian Chemical Bulletin, vol. 45, No. 3, p. 600-609.

Asscher and Vofsi, Redox Transfer. Part V. Elementary Steps. The Oxidation of Ferrous and Cuprous Chloride by Carbon Tetrachloride, 1968, Phys. Org., p. 947-952.

* cited by examiner

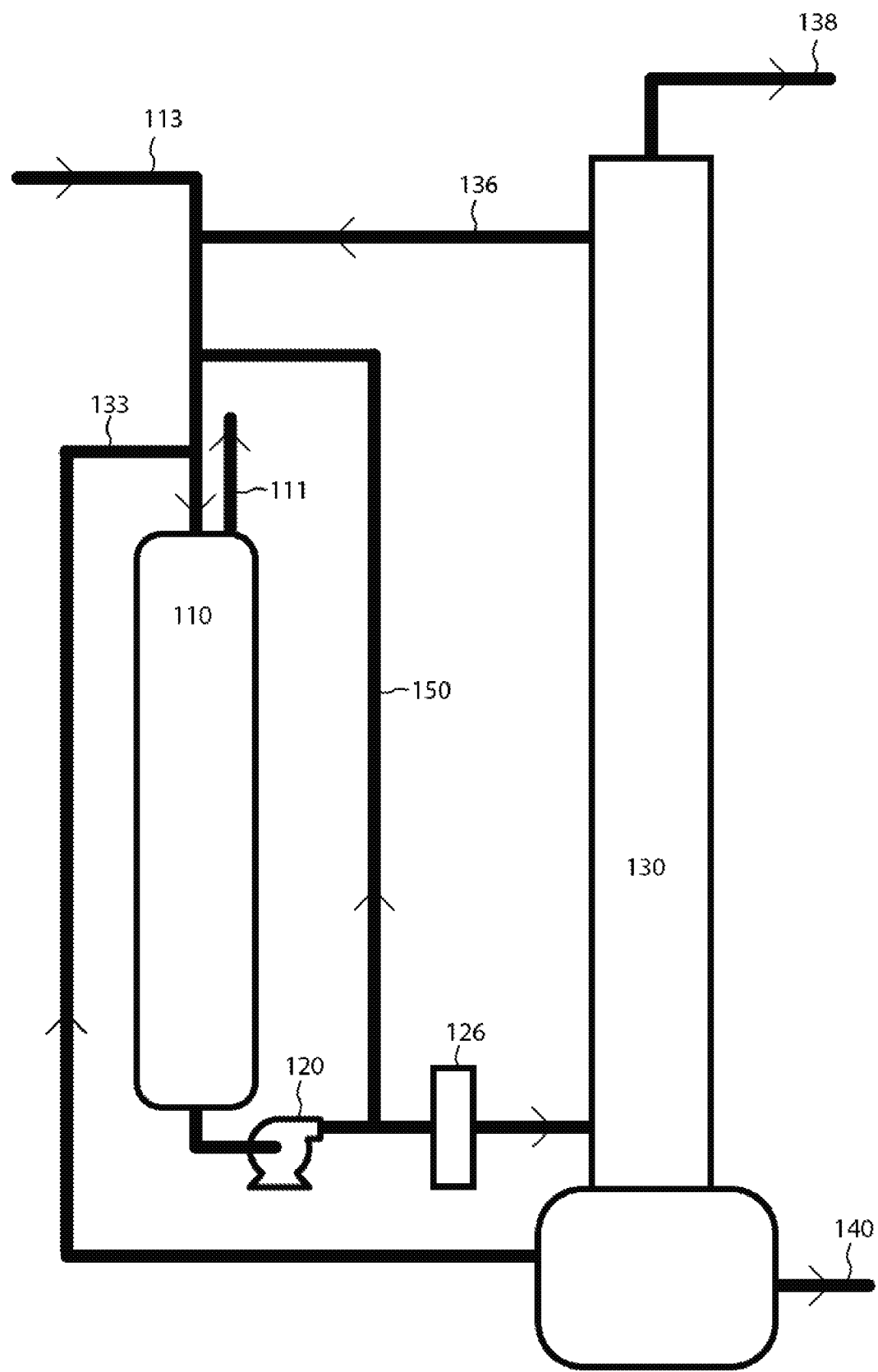

IRON SALT CATALYST REGENERATION

Iron salt catalyzed Kharasch coupling reactions and catalyst regeneration techniques disclosed herein may be used to extend industrial runtime and reactivate catalytic materials. Iron salt catalyzed Kharasch coupling reactions described herein may be used in the preparation of chlorinated compounds.

BRIEF DESCRIPTION OF DRAWINGS

FIG. 1 depicts process equipment from an example iron salt catalyzed Kharasch coupling reaction.

DETAILED DESCRIPTION

FIG. 1 depicts process equipment compatible with the methods described herein. Feedline 113 may be used to provide $CCl_4$, ethylene, and iron pentacarbonyl to reactor 110 which may be initially packed with iron metal and may have a vent line 111 for the removal of CO. Pump 120 allows recirculation through recirculation line 150 and supplies distillation equipment 130. Distillation equipment 130 may recycle iron containing compounds through recycle line 133. Distillation equipment 130 may recycle $CCl_4$ through recycle line 136. The gas and vapor discharge 138 may remove carbon monoxide, HCl gas, and other similarly light components. Product bottoms 140 may include $Cl_3C$—$CH_2$—$CH_2Cl$ and certain iron compounds. Filter 126 is an optional component that may be used to capture particulates.

Certain reactions described herein may produce hydrochlorocarbon chemicals. Certain reactions described herein may be characterized herein as iron salt catalyzed Kharasch coupling reactions.

By adding a liquid source of iron such as iron pentacarbonyl, catalytic iron salts may be reactivated in the system in a manner that is more practical than adding solid forms of metallic iron.

As that phrase is used herein "Kharasch catalytic iron compounds" represent those iron compounds having catalytic properties relative to the reaction:

$$CCl_4 + H_2C{=}CH_2 \rightarrow Cl_3C{-}CH_2{-}CH_2Cl$$

Kharasch catalytic iron compounds may for example be a $Fe(II)\text{-}(O{=}P(OR)_3)_n$ complex. Other Fe(II) complexes may also be Kharasch catalytic iron compounds if they exhibit catalytic activity relative to the above reaction. In evaluating whether a compound is sufficiently catalytic to be evaluated as a Kharasch catalytic iron compound the compound must have catalytic activity sufficient to produce a reaction rate of at least one tenth the reaction rate produced by the $FeCl_2$—$(O{=}P(OBu)_3)_2$ complex in Experimental Example 3 under similar conditions.

The techniques described herein may be used in continuous reactor, batch operations and semi-batch operations. In many cases the techniques described herein may be used to continue iron salt catalyzed Kharasch coupling reactions after an initial charge of Fe(0) metal has been depleted. The use of iron pentacarbonyl or its equivalents may eliminate or greatly reduce the need to stop operations and open a reactor for the purpose of replacing a spent iron metal Fe(0) catalyst. Economic and environmental advantages may be achieved through increased operation time and reduction of releases associated with catalyst replacement.

Hydrochlorocarbons, hydrochlorofluorocarbons and hydrofluorocarbons may be prepared using the techniques described herein. Further, the techniques described herein may be used in the preparation of chlorocarbons, chlorofluorocarbons and fluorocarbons.

Chlorocarbons and hydrochlorocarbons are, in themselves, useful chemicals. For example, carbon tetrachloride and tetrachloroethene (perchloroethylene) are useful solvents. 1,1,1,-trichloroethane is a useful solvent and chloroethene (vinyl chloride) is a useful monomer for the manufacture of plastics. Chlorocarbons and hydrochlorocarbons are also useful as chemical precursors for the manufacture of chlorofluorcarbons, hydrochlorofluorocarbons, hydrofluorocarbons and fluorocarbons. For example, 1,1,1-trichloroethane can be converted into 1,1,1-trifluoroethane, a propellant and refrigerant. Similarly, 1,1,1,2-tetrachloroethane can be converted to 1,1,1,2-tetrafluoroethane, also a useful refrigerant. Because of their ozone depleting properties, the use of chlorocarbons and chlorofluorocarbons is much less prevalent, with hydrochlorofluorocarbons and hydrofluorocarbons constituting the bulk of useful compounds of this class. Improvements in the preparation of hydrochlorocarbons, hydrochlorofluorocarbons, and hydrofluorocarbons is described herein, but the improvement is equally applicable to the manufacture of chlorocarbons, chlorofluorocarbons and fluorocarbons. These alternate examples may be prepared by selecting compounds with the appropriate substitution and such reaction variations should be considered within the scope of example reactions that may be improved by the present disclosure.

Higher molecular weight hydrochlorocarbons, hydrochlorofluorocarbons, and hydrofluorocarbons may be prepared by coupling a one-or-more carbon fragment with a two-or-more carbon fragment using the techniques described herein in conjunction with other known techniques such as described in *J. Am. Chem. Soc.* 69, 1100-1104 and 1105-1110 (1947).

Compounds of 3 or more carbons and at least 3 chlorine atoms that may be produced by iron salt catalyzed Kharasch coupling reactions, including $Cl_3C$—$CH_2$—$CH_2Cl$ and $Cl_3C$—$CH_2$—$CHCl_2$, may be produced by the reactions and methods disclosed herein.

For example, iron salt catalyzed Kharasch coupling reactions may be used with the techniques described herein in the following reaction to produce 1,1,1,3-tetrachloropropane:

$$CCl_4 + CH_2{=}CH_2 \rightarrow CCl_3{-}CH_2{-}CH_2Cl$$

The hydrogens on the ethylene may be substituted by other chemical groups such as chlorine, fluorine, and alkyl groups such as methyl-, ethyl-, nitrile, carboxylate-, etc. In addition, one of the chlorines on the carbon tetrachloride may be substituted by another group, such as hydrogen, halogen, alkyl (methyl-, ethyl-, etc.), nitrile and carboxylate groups. Thus, carbon chains (backbones) of more than three carbons may be prepared.

An example iron based catalytic reaction may proceed as follows:

$$CCl_4 + FeCl_2 \rightarrow \cdot CCl_3 + FeCl_3 \qquad \text{(Initiation)}$$

$$\cdot CCl_3 + H_2C{=}CH_2 \rightarrow Cl_3C{-}CH_2{-}CH_2 \cdot \qquad \text{(Propagation)}$$

$$Cl_3C{-}CH_2{-}CH_2 \cdot + FeCl_3 \rightarrow Cl_3C{-}CH_2{-}CH_2Cl + FeCl_2 \qquad \text{(Termination)}$$

Ferrous chloride, $FeCl_2$ may be produced by loading a reactor with some form of iron metal, Fe(0), such that it reacts with carbon tetrachloride to generate $FeCl_2$ in situ.

$$Fe(0) + 2CCl_4 \rightarrow Fe(II) + 2 \cdot CCl_3 \rightarrow Fe(II) + Cl_3C{-}CCl_3$$

The use of Fe(0) metal may be further advantageous. During the Initiation step of the reaction, Fe(II) is converted to Fe(III). In the Termination step, the Fe(III) is converted back to Fe(II) which makes the reaction catalytic. There are some side reactions that prevent Fe(III) from converting back to Fe(II) and the Fe(III) accumulates to the detriment of the reaction rate. However, the Fe(0) metal in the reactor is capable of reducing the Fe(III) back to Fe(II) thus keeping the reaction going.

Neither the iron metal Fe(0) nor the iron salts are very soluble in the reaction system nor are they particularly active as catalysts. The coupling reaction is aided by a solubilizing component, often called a co-catalyst or promoter, to be included in the reaction mixture. The co-catalyst promotes the conversion of the iron metal Fe(0) to the iron chloride salt as well as solubilizes the iron chloride salt into the carbon tetrachloride solvent. Such co-catalysts can be amines, nitriles and phosphorus containing compounds such as phosphites and phosphates.

Phosphates such as trialkyl phosphates, $(RO)_3P{=}O$, may be used. Triethyl phosphate and tributyl phosphate may be used as the phosphates. In such cases, the active catalyst takes the form of an $Fe(II)\text{-}(O{=}P(OR)_3)_n$ complex. More than one phosphate may be involved in the complex depending on the amount of phosphate used.

Fe(0) metal initially loaded into the reactor may be in a wide variety of known forms including iron particles, iron powder, cast iron, wrought iron, and iron wire. Example compositions include carbon steel, mild steel, pure iron, soft iron, ferrosilicon steel, and alloys containing iron such as stainless steel.

Fe(0) metal may be preloaded into the reactor for conversion into Fe(II). An initial charge of co-catalyst trialkyl phosphate may then be injected into the reactor. Once a useful concentration of $Fe(II)\text{-}(O{=}P(OR)_3)_n$ complex has accumulated, the alkene may then be injected continuously into the reactor. Product may then be removed at the rate at which it is produced. Fresh carbon tetrachloride may be continuously introduced into the reactor to replace that which is consumed in the process. The co-catalyst may be dissolved in this carbon tetrachloride stream so that it may also be continuously introduced into the reactor, or it may be injected independently. The reaction may thus be run continuously, constantly introducing carbon tetrachloride, co-catalyst and alkene and constantly withdrawing product. Along with the product, a dissolved mixture of $Fe(II)\text{-}(O{=}P(OR)_3)_n$ complex and $Fe(III)\text{-}(O{=}P(OR)_3)_n$ complex is withdrawn from the reactor and may be recycled to some extent to the reactor after separation from the product. The separation process may be by distillation.

Fe(0) as used herein generally refers to the iron compositions containing iron having an oxidation state of zero such as iron metal. Iron pentacarbonyl is a special instance of Fe(0) described herein. Instances of iron pentacarbonyl are described herein including economically advantageous uses of iron pentacarbonyl. Indications of Fe(0) described herein should be considered as potential opportunities for the use of iron pentacarbonyl. Uses of iron pentacarbonyl as a reducing agent are described herein.

Iron(II) chloride, referred to herein sometimes as $FeCl_2$, refers to both the molecule $FeCl_2$ and depending on the context, including the various reactants involved, may also refer to complexes of $FeCl_2$ including complexes of the general formula $FeCl_2\text{—}(O{=}P(OR)_3)_n$.

Iron(III) chloride, referred to herein sometimes as $FeCl_3$, refers to both the molecule $FeCl_3$ and depending on the context, including the various reactants involved, may also refer to complexes of $FeCl_3$ including complexes of the general formula $FeCl_3\text{—}(O{=}P(OR)_3)_n$.

$Fe(II)\text{-}(O{=}P(OR)_3)_n$ complex describes a range of compounds including the group of compounds characterized as $FeCl_2\text{—}(O{=}P(OR)_3)_n$ complexes in which R represents an alkyl group each instance of which may be a different alkyl group, in which n is a number that is at least one (1), and of which the $FeCl_2\text{—}O{=}P(OBu)_3$ complex is an example. Generally, as used herein, R-groups in the chemical formulas described herein represent alkyl groups each instance of which may be a different alkyl group even if no specific mention is made of whether the R-groups may represent alkyl groups.

$Fe(III)\text{-}(O{=}P(OR)_3)_n$ complex describes a range of compounds including the group of compounds characterized as $FeCl_3\text{—}(O{=}P(OR)_3)_n$ complexes in which R represents an alkyl group each instance of which may be a different alkyl group, in which n is a number that is at least one (1), and of which the $FeCl_3\text{—}O{=}P(OBu)_3$ complex is an example.

A variety of solvents including many phosphate compounds may be capable of contributing to a Kharasch catalytic iron compound or act as co-catalysts. Such co-catalysts can be amines, nitriles and phosphorus containing compounds such as phosphites, phosphates, and phosphoramides. Compounds of the general formula $(RO)_3P{=}O$ may be particularly useful with $(BuO)_3P{=}O$ being an example composition. Phosphates that may be used in the processes described herein may include trimethyl phosphate, triethyl phosphate, tripropyl phosphate, and tributyl phosphate. Phosphates of higher molecular weights may also be used. Hexamethylphosphoramide is an example of a phosphate amide that may be used as such a solvent.

Compositions such as represented by the general formula $Y\text{—}CCl_3$ wherein Y is selected from hydrogen, halogen, alkyl group, nitrile, and carboxylate may be subjected to the iron salt catalyzed Kharasch coupling reactions with olefins as described herein and $CCl_4$ is an example compound used herein to illustrate the process. Examples using $CCl_4$ herein should also be understood to include examples of a broader group of compounds represented by the formula $Y\text{—}CCl_3$.

Alkenes described herein generally represent unsaturated hydrocarbons such as ethylene, but halogen substituted alkenes such as chloroethene (vinyl chloride) may be used. In such situations, the group of halogen substituted alkenes matching the alkene composition or alkene general formula described should be considered as alternate examples that may be used as described.

Iron pentacarbonyl $Fe(CO)_5$ may be used as a liquid substitute for the iron metal, Fe(0), to maintain or regenerate catalyst activity in reaction systems. The introduction of iron pentacarbonyl may eliminate the need to stop the reaction and open the reactor for the replacement of spent catalyst.

In one embodiment, a continuous reactor performing an iron salt catalyzed Kharasch coupling reaction of, for example, carbon tetrachloride and ethylene, having spent its charge of metal Fe(0) may be continuously reactivated by the injection of iron pentacarbonyl $Fe(CO)_5$. Co-solvents such as tributyl phosphate $(BuO)_3P{=}O$ may be co-injected. The Fe(0) from the $Fe(CO)_5$ reduces inactive Fe(III) back to active Fe(II) catalyst initiator. For example, a $FeCl_3$ complex may be converted back to an active initiating catalytic $FeCl_2$ complex. During this process, the Fe(0) of $Fe(CO)_5$ may be oxidized to Fe(II) and the CO molecules are shed according to the following reaction:

$$Fe(0)+2Fe(III) \rightarrow Fe(II)+2Fe(II)$$

or more specifically, $$Fe(CO)_5 + 2FeCl_3 \rightarrow 3FeCl_2 + 5CO$$

The $FeCl_3$ is present in the form of a co-solvent complex having the general formula $FeCl_3$—$(O=P(OR)_3)_n$ and the regenerated $FeCl_2$ is in the form of a co-solvent complex having the general formula $FeCl_2$—$(O=P(OR)_3)_n$. To maintain a high level of solubility, the molecule of $FeCl_2$ that is generated from the $Fe(CO)_5$ may be solvated with additional tributyl phosphate.

$Fe(CO)_5$ may undergo a partial or complete ligand exchange of co-solvent for CO. In the case of tributyl phosphate, the initial reaction, where CO is off-gassed may be:

$$Fe(CO)_5 + (BuO)_3P=O \rightarrow (BuO)_3P=O-Fe(CO)_4 + CO\uparrow$$

By the time the $Fe(CO)_5$ is converted to $FeCl_2$, all the CO ligands are released. This reaction is demonstrated by the quantitative evolution of CO in the Example reactions described below.

In one embodiment of a spent iron salt catalyzed Kharasch coupling reaction, ½ molar equivalent of $Fe(CO)_5$ is injected for every equivalent of $FeCl_3$ that is desired to be reduced to $FeCl_2$. It is not necessary to allow the coupling catalyst to become completely spent. Iron pentacarbonyl, $Fe(CO)_5$, may be continuously injected at a rate that approximates the rate at which the catalyst is deactivating such that the catalyst maintains a constant level of activity. In certain cases, the injection of $Fe(CO)_5$ may begin when the supply of solid Fe(0) in the reactor is nearing depletion. In other cases, the injection of $Fe(CO)_5$ may be provided over the course of the operations not waiting for the depletion of Fe(0) metal. $Fe(CO)_5$ may, for example, be added when the reaction rate falls below a predetermined threshold reaction rate.

Iron pentacarbonyl may be used in an economically effective way by coupling its use with that of one of the several forms of Fe(0) such as iron filings or wire. Such use may proceed by initially including a substantial charge of solid Fe(0) in a reactor and allowing significant consumption of the solid Fe(0) either prior to the introduction of iron pentacarbonyl or during the introduction of iron pentacarbonyl. In the context of the reactions described herein, a portion of the iron pentacarbonyl supplied to the reactor may be supplied to the reactor after at least half of the available solid Fe(0) in the reactor has been consumed. As that phrase is used herein "native consumable Fe(0) metal" designates metallic iron located in a reactor as a reagent having an oxidation state of zero and having a concentration of at least 10 grams per liter of reactor volume.

In a related embodiment, the off-gassed CO may be continuously removed from the system as it is formed. Purification of the chlorocarbon product along with potential recovery of the catalyst may be achieved in a distillation column. The off-gassed CO may be removed from the head space of the reactor and/or by one or more distillation columns, being taken off in the "non-condensables" stream which may also carry HCl gas and the like.

As described in the reactions herein, $Fe(CO)_5$ does not function directly as a catalyst. Rather it is a material input that ultimately functions as a reducing agent to regenerate spent catalyst, that is convert Fe(III) back to Fe(II).

While $Fe(CO)_5$ may be more expensive than Fe(0) metal it operates simultaneously to regenerate Fe(III) into active catalyst and in the process contributes to the creation of new active catalyst.

Other carbonyls of Fe(0) exist and may be used for potential catalyst regeneration in the processes described herein. $Fe_2(CO)_9$ and $Fe_3(CO)_{12}$ have potential for such use. Both $Fe_2(CO)_9$ and $Fe_3(CO)_{12}$ are sparingly soluble in most organic solvents, so they may be used as a source of Fe(0) using the techniques described herein including for example in solutions of $CCl_4$. Examples using $Fe(CO)_5$ described herein should also be understood to include the alternate examples of the above referenced carbonyls of Fe(0).

It should be pointed out for clarity, that in addition to iron pentacarbonyl (aka iron carbonyl), there is a material called carbonyl iron. Carbonyl iron is a finely divided iron powder used to manufacture the iron cores of high frequency magnetic coils for televisions and radios, among other uses. Carbonyl iron is manufactured from iron pentacarbonyl resulting in the similar name. Carbonyl iron plays no role in the reactions described herein.

EXPERIMENTAL EXAMPLES

In the following experimental examples, all chemicals were reagent grade from Aldrich Chemical Corp. Carbon tetrachloride 99.9% and tributyl phosphate 97% were distilled before use. Iron(III) chloride 97% and iron pentacarbonyl 99.9+% were used as received. Ethylene was 99.99%. Reactions were performed in an oven dried and $N_2$ purged 250 mL glass pressure vessel affixed with valves for the introduction of reagents, a pressure gauge and an automatic pressure relief valve set at 100 psig. The vessel was heated in a temperature-controlled oil bath. Stirring was achieved with a Teflon coated magnetic stir bar. Reaction products were washed with 10% HCl, dried with $MgSO_4$ and analyzed on a Varian 3800 Gas Chromatograph with a 60 meter DB-1701 column. Evolved CO gas was captured by water displacement in an inverted 1000 mL graduated cylindrical reservoir.

Experimental Example 1

Comparative—$FeCl_3$ Alone 4.87 g (0.03 mol) $FeCl_3$ was charged to a 250 mL glass pressure vessel. 96.5 mL (1.0 mol) $CCl_4$ and 8.2 mL (0.03 mol) $(BuO)_3P=O$ were then charged. The system was purged with ethylene gas to displace the $N_2$. The reactor was then warmed to 80° C. and ethylene was charged to 60 psig. The reaction was run for 9 hours under a continuous ethylene pressure of 60 psig. The reactor was cooled, and the remaining pressure released. Gas chromatographic analysis showed the final composition to be 100% $CCl_4$, that is, no reaction had occurred.

Experimental Example 2

Comparative—$Fe(CO)_5$ Alone 96.5 mL (1.0 mol) $CCl_4$ and 16.3 mL (0.06 mol) $(BuO)_3P=O$ were charged to a 250 mL glass pressure vessel. 3.94 mL (0.03 mol) $Fe(CO)_5$ was injected by syringe and the reaction stirred 15 minutes with no discernable reaction. The system was slowly heated whereupon at about 65° C. the pressure began to rise. When the temperature was 68° C. and the pressure reached 40 psig, the reactor was continuously vented of CO pressure. Venting was continued until CO was no longer evolving whereupon all pressure was vented. A total of about 3420 mL of CO gas was collected. The reactor was then warmed to 80° C. and ethylene was charged to 60 psig. The reaction was run under a continuous ethylene pressure of 60 psig. After 8 hours, the reactor was cooled, and the remaining pressure released. Gas chromatographic analysis showed the final product to be 42.5% 1,1,1,3-tetrachloropropane, 39.3% $CCl_4$, and 9.8% $C_2Cl_6$.

Experiential Example 3

($Fe(CO)_5$ Reactivating $FeCl_3$):

3.24 g (0.02 mol) $FeCl_3$ was charged to a 250 mL glass pressure vessel. 96.5 mL (1.0 mol) $CCl_4$ and 16.3 mL (0.06 mol) $(BuO)_3P\!\!=\!\!O$ were then charged. 1.31 mL (0.01 mol) $Fe(CO)_5$ was injected by syringe and the reaction stirred 15 minutes. Visible CO evolution began immediately. The system was slowly heated. When the temperature was 43° C. and the pressure reached 40 psig, the reactor was continuously vented of CO pressure. Venting was continued until CO was no longer evolving whereupon all pressure was vented. A total of about 1140 mL of CO gas was collected. The reactor was then warmed to 80° C., and ethylene was charged to 60 psig. The reaction was run under a continuous ethylene pressure of 60 psig. After 8 hours, the reactor was cooled, and the remaining pressure released. Gas chromatographic analysis showed the final product to be 44.8% 1,1,1,3-tetrachloropropane, 30.0% $CCl_4$, and 4.4% $C_2Cl_6$.

TABLE 1

G.C. Results of Experimental Examples 1-3.

| Experimental Example | Reagents | $CCl_4$ | 1,1,1,3-Tetrachloropropane | $C_2Cl_6$ |
|---|---|---|---|---|
| 1 | $FeCl_3$ | 100 | 0 | 0 |
| 2 | $Fe(CO)_5$ | 39.3 | 42.5 | 9.8 |
| 3 | $Fe(CO)_5$ + $FeCl_3$ | 30.0 | 44.8 | 4.4 |

Chemical processes described herein may, for example, comprise reacting a reagent of the general formula Y—$CCl_3$ with an alkene in a reactor thereby producing a halogenated hydrocarbon; wherein iron pentacarbonyl is present during the reacting of the reagent of the general formula Y—$CCl_3$ with an alkene; wherein a compound selected from $FeCl_3$ and a $FeCl_3$ complex is removed from the reactor, subjected to separation, and returned to the reactor; wherein the reagent of the general formula Y—$CCl_3$ is added to the reactor during the reacting of the reagent of the general formula Y—$CCl_3$ with the alkene; wherein the iron pentacarbonyl is added to the reactor during the reacting of the reagent of the general formula Y—$CCl_3$ with the alkene; and wherein Y is selected from hydrogen, halogen, alkyl group, nitrile, and carboxylate. In a related example, a phosphate compound may be added to the reactor during the reacting of the reagent of the general formula Y—$CCl_3$ with the alkene. In a related example, the reagent of the general formula Y—$CCl_3$ is $CCl_4$. In a related example, the halogenated hydrocarbon may be a hydrochlorocarbon.

Chemical processes described herein may, for example, comprise loading a reactor with a quantity of Fe(0) metal; supplying $CCl_4$ to the reactor; supplying a phosphate compound to the reactor; supplying an alkene to the reactor; and supplying a carbonyl of Fe(0) to the reactor; wherein a chemical reaction in the reactor produces a halogenated hydrocarbon. In a related example, a portion of the carbonyl of Fe(0) supplied to the reactor may be supplied to the reactor after greater than half of the quantity of Fe(0) metal has been consumed. In a related example, the phosphate compound may be a trialkyl phosphate. In a related example, the carbonyl of Fe(0) may be iron pentacarbonyl. In a related example, the alkene is selected from ethylene, propylene, butylene, chloroethylene, 1,1-dichloroethylene, 1,2-dichloroethylene, trichloroethylene, tetrachloroethylene, fluoroethylene, 1,1-difluoroethylene, 1,2-difluoroethylene, trifluoroethylene, tetrafluoroethylene, 1-chloro-1-fluoroethylene, 1-chloro-2-fluoroethylene, 1,1-dichloro-2-fluoroethylene, 1,2-dichloro-1-fluoroethylene, 1,1,2-trichloro-2-fluoroethylene, 1-chloro-1,2-difluoroethylene, 1-chloro-2,2-difluoroethylene, and 1-chloro-1,2,2-trifluoroethylene. In a related example, related other mixed chlorofluoroethylenes may be used. In a related example, the chemical reaction occurs in the presence of a Kharasch catalytic iron compound.

Chemical processes described herein may, for example, comprise conducting an iron salt catalyzed Kharasch coupling reaction; wherein the iron salt catalyzed Kharasch coupling reaction occurs in the presence of iron pentacarbonyl; wherein iron atoms from the iron pentacarbonyl are oxidized during the iron salt catalyzed Kharasch coupling reaction; wherein iron atoms from a compound selected from $FeCl_3$ and an $FeCl_3$ complex are reduced during the iron salt catalyzed Kharasch coupling reaction; and wherein the iron salt catalyzed Kharasch coupling reaction occurs in the presence of a native consumable Fe(0) metal. In a related example, the iron salt catalyzed Kharasch coupling reaction may occur in the presence of a Kharasch catalytic iron compound. In a related example, the iron salt catalyzed Kharasch coupling reaction may occur in the presence of a phosphate compound. In a related example, the iron salt catalyzed Kharasch coupling reaction may occur in the presence of a trialkyl phosphate. In a related example, the iron salt catalyzed Kharasch coupling reaction may occur in the presence of a reaction of the iron pentacarbonyl with the compound selected from $FeCl_3$ and an $FeCl_3$ complex.

Chemical reactors described herein may, for example, comprise a vessel; a quantity of iron carbonyl within the vessel; a quantity of native consumable Fe(0) metal within the vessel; a quantity of $CCl_4$ within the vessel; a quantity of a $FeX_2$—$(O\!\!=\!\!P(OR)_3)_n$ complex within the vessel; a quantity of $FeX_3$—$(O\!\!=\!\!P(OR)_3)_n$ complex within the vessel; a quantity of alkene in the vessel; and a quantity of a halogenated hydrocarbon having at least three carbons within the vessel; wherein R is an alkyl group each instance of which may be a different alkyl group; wherein X is a halogen, wherein Y is selected from hydrogen, halogen, alkyl group, nitrile, and carboxylate; and wherein n is a positive number. In a related example, the iron carbonyl may be iron pentacarbonyl. In a related example, n may be selected from 1 and 2.

The above-described embodiments have a number of independently useful individual features that have particular utility when used in combination with one another including combinations of features from embodiments described separately. There are, of course, other alternate embodiments which are obvious from the foregoing descriptions, which are intended to be included within the scope of the present application.

The invention claimed is:

1. A chemical process comprising:
   a. reacting a reagent of the general formula Y—$CCl_3$ with an alkene in a reactor thereby producing a halogenated hydrocarbon;
   b. wherein iron pentacarbonyl is present during the reacting of the reagent of the general formula Y—$CCl_3$ with an alkene;
   c. wherein a compound selected from $FeCl_3$ and a $FeCl_3$ complex is removed from the reactor, subjected to separation, and returned to the reactor;

d. wherein the reagent of the general formula Y—CCl₃ is added to the reactor during the reacting of the reagent of the general formula Y—CCl₃ with the alkene;
e. wherein the iron pentacarbonyl is added to the reactor during the reacting of the reagent of the general formula Y—CCl₃ with the alkene;
f. wherein Y is selected from hydrogen, halogen, alkyl group, nitrile, and carboxylate; and
g. wherein a majority of iron pentacarbonyl added to the reactor reacts according to the equation $$Fe(CO)_5 + 2FeCl_3 \rightarrow 3FeCl_2 + 5CO.$$

2. The chemical process of claim 1 wherein a phosphate compound is added to the reactor during the reacting of the reagent of the general formula Y—CCl₃ with the alkene.

3. The chemical process of claim 1 wherein the reagent of the general formula Y—CCl₃ is CCl₄.

4. The chemical process of claim 1 wherein the halogenated hydrocarbon is a hydrochlorocarbon.

5. A chemical process comprising:
a. loading a reactor with a quantity of Fe(0) metal;
b. supplying CCl₄ to the reactor;
c. supplying a phosphate compound to the reactor;
d. supplying an alkene to the reactor;
e. supplying a carbonyl of Fe(0) to the reactor;
f. reacting a portion of the Fe(0) metal to a quantity to FeCl₃;
g. reacting most of the carbonyl of Fe(0) supplied to the reactor with a portion of the quantity to FeCl₃ producing CO and FeCl₂;
h. wherein a chemical reaction in the reactor produces a halogenated hydrocarbon.

6. The chemical process of claim 5 wherein a portion of the carbonyl of Fe(0) supplied to the reactor is supplied to the reactor after greater than half of the quantity of Fe(0) metal has been consumed.

7. The chemical process of claim 5 wherein the phosphate compound is a trialkyl phosphate.

8. The chemical process of claim 5 wherein the carbonyl of Fe(0) is iron pentacarbonyl.

9. The chemical process of claim 5 wherein the alkene is selected from ethylene, propylene, butylene, chloroethylene, 1,1-dichloroethylene, 1,2-dichloroethylene, trichloroethylene, tetrachloroethylene, fluoroethylene, 1,1-difluoroethylene, 1,2-difluoroethylene, trifluoroethylene, tetrafluoroethylene, 1-chloro-1-fluoroethylene, 1-chloro-2-fluoroethylene, 1,1-dichloro-2-fluoroethylene, 1,2-dichloro-1-fluoroethylene, 1,1,2-trichloro-2-fluoroethylene, 1-chloro-1,2-difluoroethylene, 1-chloro-2,2-difluoroethylene, and 1-chloro-1,2,2-trifluoroethylene.

10. The chemical process of claim 5 wherein the chemical reaction occurs in the presence of a Kharasch catalytic iron compound.

11. A chemical process comprising:
a. conducting an iron salt catalyzed Kharasch coupling reaction;
b. wherein the iron salt catalyzed Kharasch coupling reaction occurs in the presence of iron pentacarbonyl;
c. wherein iron atoms from the iron pentacarbonyl are oxidized during the iron salt catalyzed Kharasch coupling reaction;
d. wherein iron atoms from a compound selected from FeCl₃ and an FeCl₃ complex are reduced during the iron salt catalyzed Kharasch coupling reaction; and
e. wherein the iron salt catalyzed Kharasch coupling reaction occurs in the presence of a native consumable Fe(0) metal.

12. The chemical process of claim 11 wherein the iron salt catalyzed Kharasch coupling reaction occurs in the presence of a Kharasch catalytic iron compound.

13. The chemical process of claim 11 wherein the iron salt catalyzed Kharasch coupling reaction occurs in the presence of a phosphate compound.

14. The chemical process of claim 11 wherein the iron salt catalyzed Kharasch coupling reaction occurs in the presence of a trialkyl phosphate.

* * * * *